United States Patent [19]

Lambert

[11] Patent Number: 5,267,974
[45] Date of Patent: Dec. 7, 1993

[54] HYPODERMIC SYRINGE WITH FOAM SPONGE RESERVOIR

[76] Inventor: William S. Lambert, 52 Tokalon, Metairie, La. 70001

[21] Appl. No.: 893,526

[22] Filed: Jun. 4, 1992

[51] Int. Cl.[5] .............................................. A61M 5/32
[52] U.S. Cl. ...................... 604/195; 604/192; 604/212; 604/216
[58] Field of Search ............... 604/192, 195, 197–199, 604/212–216, 239

[56] References Cited

U.S. PATENT DOCUMENTS

| | | | |
|---|---|---|---|
| 2,403,074 | 7/1946 | Goldsmith | 604/195 |
| 2,673,561 | 3/1954 | Peterson, Jr. | 604/216 |
| 2,696,212 | 12/1954 | Dunmire | 604/216 X |
| 2,769,443 | 11/1956 | Dunmire | 604/212 X |
| 2,792,835 | 5/1957 | Ferguson | 604/212 |
| 2,944,549 | 7/1960 | Alexander | 604/212 X |
| 3,094,988 | 6/1963 | Dunmire | 604/197 X |
| 4,392,859 | 7/1983 | Dent | 604/198 |
| 4,666,436 | 5/1987 | McDonald et al. | 604/198 |
| 4,775,363 | 10/1988 | Sandsdalen | 604/110 |
| 4,795,432 | 1/1989 | Karczmer | 604/110 |
| 4,883,068 | 11/1989 | Dechow | 128/760 |
| 4,919,652 | 4/1990 | Alter et al. | 604/110 |

Primary Examiner—C. Fred Rosenbaum
Assistant Examiner—Corrine Maglione

[57] ABSTRACT

A safely-disposable, one-use limited, sealingly-enveloped, injectant-saturated, elastic foam sponge, axially encompassing a hypodermic cannula, depressably slidable there-thru for simultaneous, subcutaneous tissue injection.

3 Claims, 3 Drawing Sheets

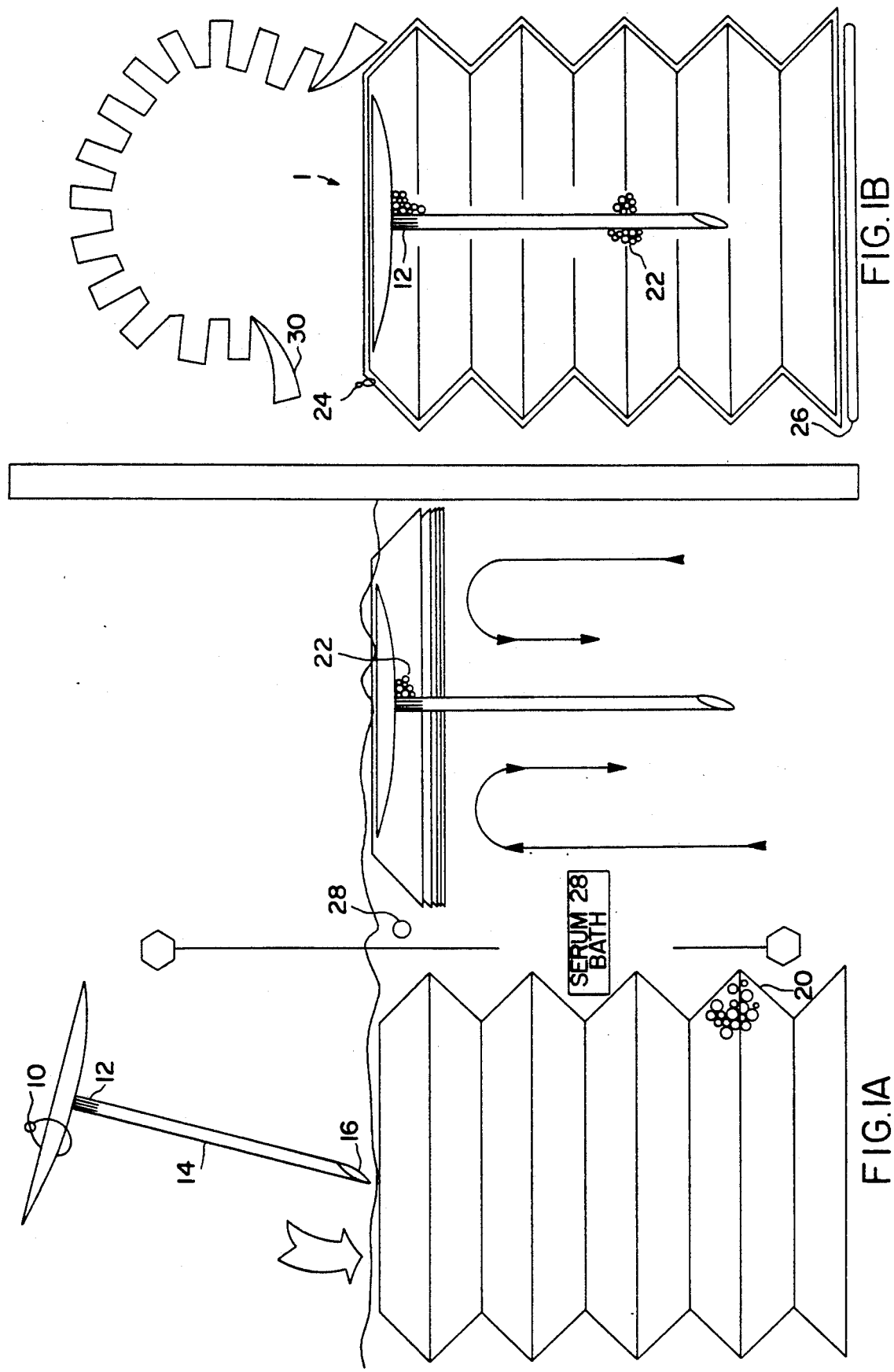

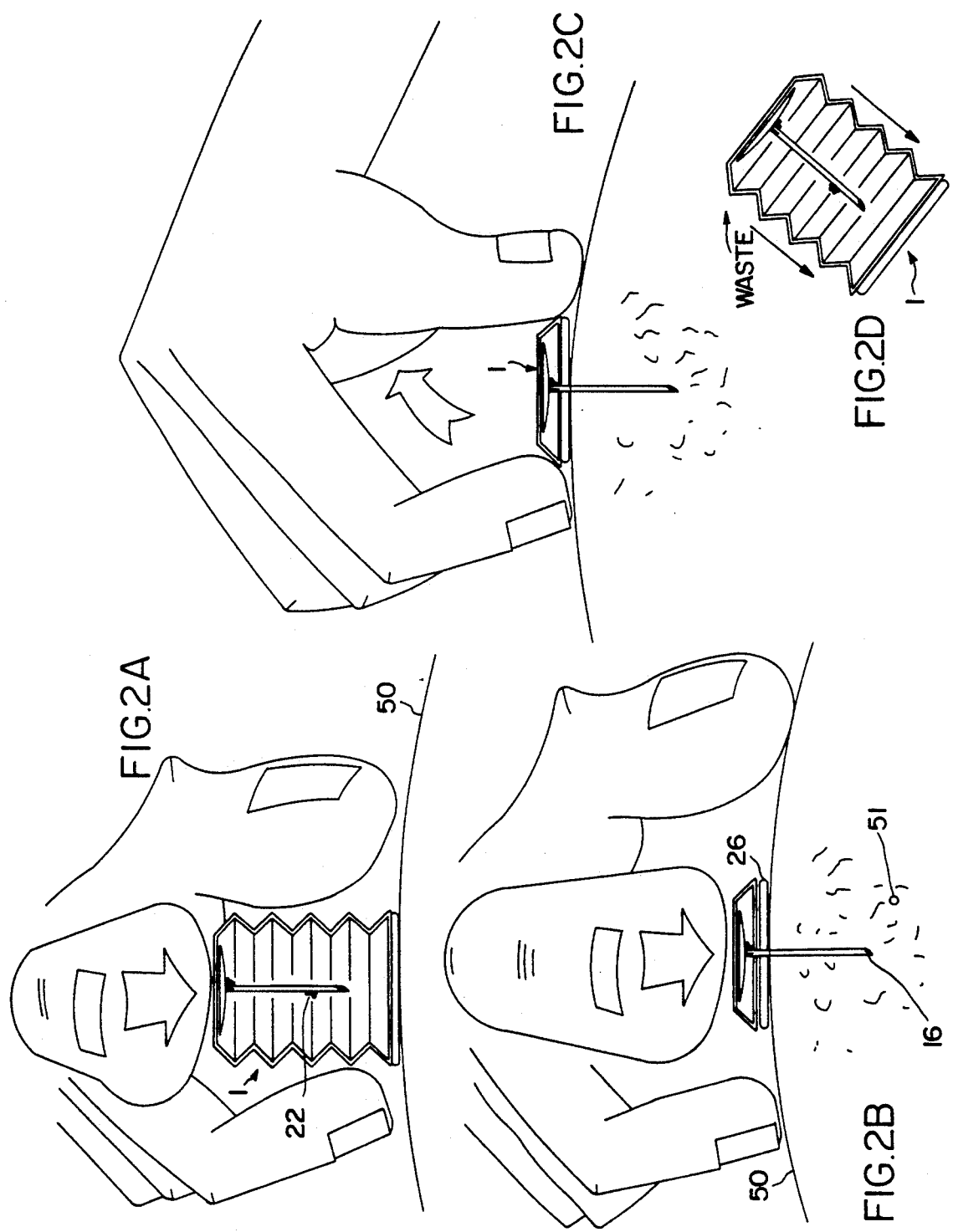

5,267,974

HYPODERMIC SYRINGE WITH FOAM SPONGE RESERVOIR

CROSS-REFERENCE TO RELATED APPLICATION

Ser. No. 07/605,153, Fail Safe Composite Hypodermic Syringe with Reversible Needle and Guard Assembly, NOTICE-OF-ALLOWANCE dated Feb. 26, 1992 U.S. Pat. No. 5,163,908—Mr. ADAM CERMAK, EXAMINER, GAU 3306

BACKGROUND OF INVENTION

Field of Invention
medical equipment—disposable hypodermic syringes
Description of the Related Art The reluctant incapacity for self-injection by Every-Man aside, hypodermic manufacturers have long sought a reliable one-use limitation design re drug-addict needle-sharing contagion, as well as a mechanical component deterrent to "accidental sticks" by Health-Care personnel. Disease transmission from both sources is rampant in 1992.

The present industry standard is an extruded semi-rigid tubular reservoir, receivable of a sliding-plunger to both vacuum fill and then eject a fluid through a sharpened hollow needle.

While technically no Art appropriately applies, some focus on offering accidental needle point stick protection alone, per manipulation of sheaths and sleeves, appearing complicated to manufacture, inconvenient, and suggestive of unreliability. Prior Art is physically incapable of providing the undisturbed needle sterility of the instant. Other Art singularly addresses needle-sharing, which is structurally impossible with instant. Factually, none physically provide them together in the same instrument. In standard, regular maintenance, and/or emergency dosage injections, i.e., diabetic insulin, tetanus, morphine, etc., the convenient pre-loads of the instant eliminate many steps as well as those potential negatives of the normal serum-ingestion, charging-phase as required immediate-to-injection as is mandatory for known Art.

SUMMARY OF THE INVENTION

This compact, two-element, poly-plastic hypodermic injector, physically implemental, synergetic improvement to this field that can be compared, functionally, to the poison injection, fang implantation in the manner of the common rattle-snake bite.

A typical, early morning scenario could be a palsied elder person, gingerly fumbling in the dim refrigerator light to de-package and fill a syringe to a correctly-read dosage, accurately insert needle, and self inject serum. And then hazardously re-cap the needle with safe discard of the spent, contaminated ensemble, all subject to those typical errors of vision and dexterity peculiar to this particular process.

Another scenario could be on-location of human emergencies where masses, incapable of even the above process of self-injection of standard fixed-dosages, must wait-in-line indefinitely for such injections, as, of practical necessity, administered by others.

The prime object of instant is simplicity, as reflected in its efficient, inexpensive manufacture, preparation for, actual injection, and safe disposal design. Economically accessible by healthcare professionals, as well as to all consumers: the young, old, arthritic, infirm, and even the Blind. At-will self-injection is now accessible by those motor-skill impaired to whom the operation of the known Art is physically unmanageable. Projected damage survival from dropped impact is not comparable to Prior Art.

A further object is the assured 100%, uninterrupted manufacture-to-disposal sterility. The metal or plastic needle is post-injection protected for proper safe disposal per the re-extended reservoir foam sponge housing. Singular contamination exposure, even to air, exists only on actual body tissue penetration.

Object of one-time use-limitation is insured by the structural impossibility for creation of a compounded internal vacuum infusion within reservoir, as-likened to the requirement of externally-forced infusion of a childs' balloon. Each of these units represents one less re-usable needle on the Streets to be shared.

Accidental sticks are eliminated by this full-time needle protection. Lateral, linear support of the needle shaft by the encompassment of the guarding foam sponge is as comparable to a human index finger encompassed within the opposite fist.

Instant eliminates the traditional provisional disinfectant pre-swabbing phase of every living tissue injection along with the cumulative professional medical expense thereof. After application of a sealing skin over the surface of foam sponge media, a stick-on, strip-a-way, germicide-saturated foam gum pad is attachable to outer bottom surface of the instant for pre-penetration contactive disinfection of the injection site immediate to needle penetration of tissue. Needle disinfectantly "self wipes" on post-injection extraction back thru pad.

Optionally self-adhesively attachable to the top end surface of the unit, is a spring-grip finger-ring for additional digital manipulative stability, i.e., arthritis, palsy, and the otherwise impaired.

Inexpensive manufacture, consumer acquisition, a variety of optional utilization methods, insured, isolated 100% sterility, assured one-use limitation, accidental-stick protection, safely disposable, and constitutes a compact serum reservoir component that is, in one article, a plunger, syringe, and needle guard. Simplicity facilitates these injections. An unseen needle causes no needle-fright.

DETAILED DESCRIPTION OF THE DRAWINGS

FIG. 1A is a side view of assembly-line production of an accordion-like segment of a resilient, deformable, porous media such as a mini-celled foam sponge immediate to being centrally-penetrated to fully seat a formed standard hypodermic needle while simultaneously being maximally, contractively-compressed to allow maximum void-free, sub-surface serum dosage absorption/saturation occurring upon coincidental re-expansion to original configuration.

FIG. 1B showing providing lateral, vertical, and plumb, conductable needle support, the foam sponge media is either, by formulation, "self-skinning" per U/V light-exposure curing or, comprehensively sealed via the so-called, plastic "shrink-wrapping" process. Either is then immediately injection-ready. A stick-on, strip-to-contact, pre-penetration, contactive-disinfectant foam gum pad is attachable to the outer bottom face of instant article. Same is minimally adherable to tissue surface, facilitating disinfection and offering conductive stability. Also optionally factory-attachable, for additional control to aid the digitally-impaired, is the self-adhering, flared free-ends of a flexible plastic fitz-all, spring-grip, finger-ring holder.

FIG. 2A portrays the instant article digitally-applied, snugly against the tissue injection site prior to injector-actuation.

FIG. 2B shows the digital depression-actuation of the serum injection into the subdermal tissue.

FIG. 2C depicts the communication of the thumb and index finger to snatch-out the spent article, the rebounding foam media laterally re-encompassing and protectively isolating the contaminated needle.

FIG. 2D shows spent article/ensemble, safe for disposal.

Figure 3D:
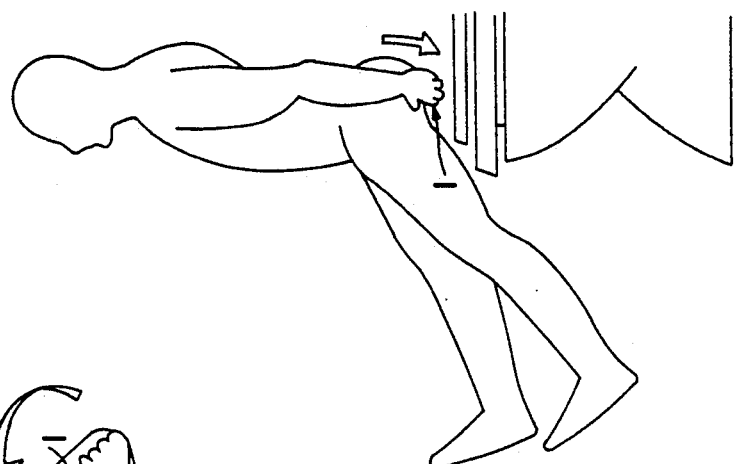
Figure 3C:
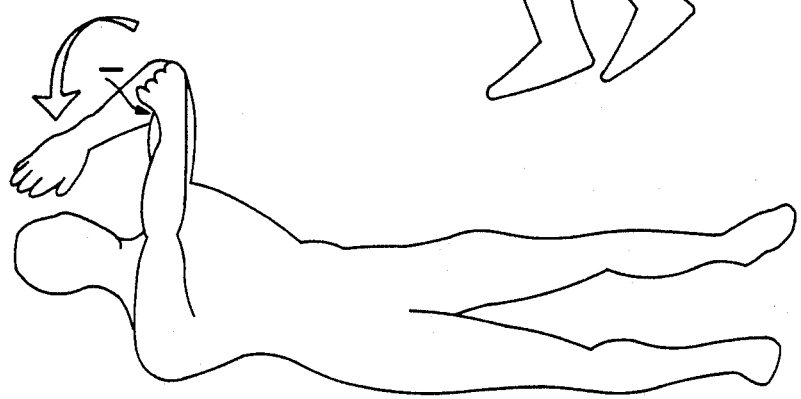
Figure 3B:
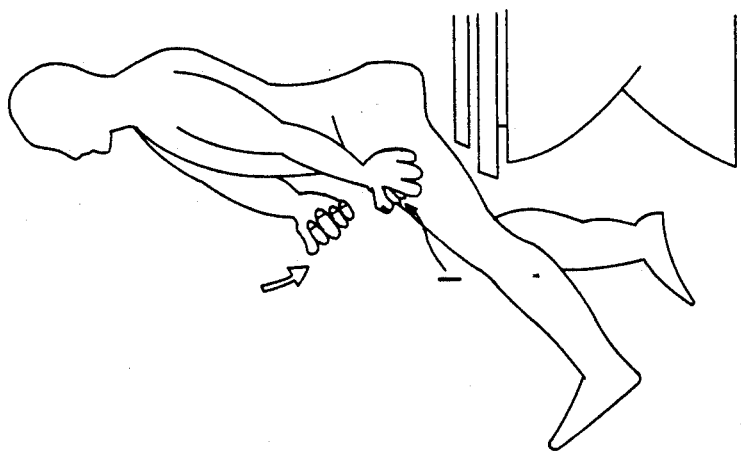
Figure 3A:
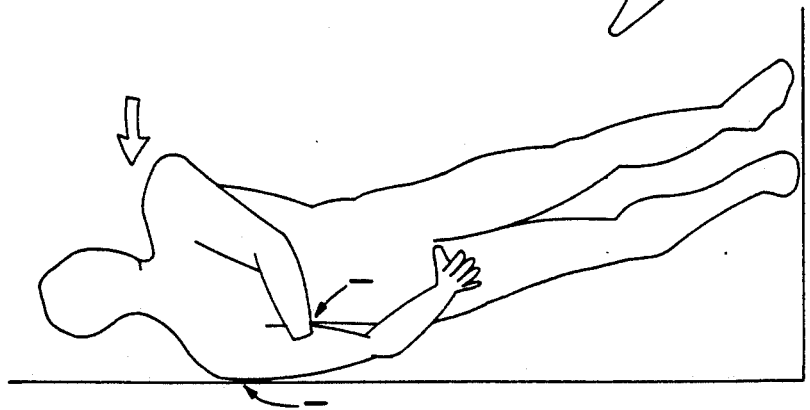

FIG. 3A suggests a gentle lunge against a wall to facilitate compressive pressure injection into either inner, or outer surface of upper arm as article is so digitally-positioned thereon.

FIG. 3B depicts injection/implantation, as-preferred, applicable to the subdermal tissue of the upper thigh as so digitally-positioned.

FIG. 3C shows rapid, clam-shell, compressive closing-action facilitating injection as article is digitally-located in the crook of the arm.

FIG. 3D displays the instant article compressively sandwiched between an unyielding surface and against the gluteus maxima to force implantation of the serum contents therein.

DRAWING REFERENCE NUMERALS 1 article of invention in toto
10 composite standard needle element with needle-shaft shoulder-bell, so-flared
12 serum-inlet side-splits formed in upper needle-shaft 14
14 needle-shaft portion of needle composite 10
16 needle-point and discharge outlet
20 accordion-compressible, uniformly-celled, foam sponge media element
22 laterally, linear, conduction-guidance effect of foam cells of 20
24 sealed, serum-containment envelope
26 adhesively-attachable, disinfectant pad/disc
28 serum-injectant per absorption-saturation bath-/filling of 20 media
30 finger-ring free-ends adhesively self-attachable to topmost of 1
50 epidermis surface site to-be-injected
51 serum-spread implantation of subcutaneous body tissue

DETAILED DESCRIPTION OF PREFERRED EMBODIMENT

Preferred element descriptions exhibited as in-assembly and as in a typical utilization:

Reference numeral 1 refers to the complete instant article.

The main body is represented by a segment of poly-plastic, resilient, maximally absorbable, non-disintegrating, mini-celled 22 foam sponge media 20, dimensioned and color-coded per dosage, as absorbingly-saturated with that quantity of injectant 28.

A sequentially-collapsing, non-critically accordion-like, cylindrical configuration 20, is apparently the most efficient, as-selected over ball-shape, straight-sided, tapered, bulbous, etc.

Needle composite 10 is concentrically, penetratingly-seated into top-end portion of foam sponge media 20. Needlepoint 16 is centrally-encompassed, in sterility, there within by the lower end-portion of 20 FIG. 1B.

Measured-exposure of Ultra-Violet light transforms the outer surface of the serum-saturated, open-celled, so-formulated foam-media 20 outer surface to render a self-healingly perforable, "self-skinning", flexible, sealed, outer surface envelope 24, or shrink-wrapped in high-tensile plastic sealing film.

Conductive, laterally supported guidance 22 is provided needle by deformably-flexible foam sponge 20, encompassing the centrally-mounted, metal or plastic standard needle ensemble 10. Same is comprised of a needlepoint discharge outlet 16, hollow needle shaft 14 and including formed upper needle inlet side vents 12 therein with a flared shoulder-bell, as-flattened to facilitate uniformly-spread compression of 20 for serum injection thru needlepoint 16.

Presuming appropriate dosage, needle length, and I.D./O.D., unit is digitally-positioned FIG. 2A as foam gum pad 26 disinfectantly contacts pre-injection site epidermis surface 50.

As shown in FIG. 2A, immediate to penetration/-serum-release, progressive depression increases and compounds reservoir 20 internal pressure, as comprehensively constrained by skin/envelope 24.

Simultaneous compressive-closing and needlepoint penetration 16 FIG. 2B thru reservoir 20 bottom end-face, and into subdermal tissue, forces implantation 51 of prescribed serum 28 dosage saturation therein.

Dosage totally implanted in FIG. 2C with voided reservoir maximally-compressed, spent article 1 is disengaged, re-extending naturally in FIG. 2D to pre-deformation configuration, protectively re-encompassing contaminated needlepoint 16, stick-prevention continuing thru to safe, protected disposal.

A unit comprising efficient, compact simplicity, sterility, variable modes of utilization, absent needle-fright, protected disposal, inexpensive manufacture and provision to consumers of no-stick, no-share, maximal safety, and efficiency.

I claim:

1. A dosage-dimensionable, composite, safely disposable, self-injectable hypodermic syringe, comprising:
a minimally thin-skinned, hermetically sealable, resilient film-envelope, precisely formulated self-healingly, to effect a radially-contracting, transverse, liquid seal around the periphery of an axially penetratable cannula;
a cylindrical, injectant-saturated, absorbingly open-celled, reconformably collapsible, elastic, semi-rigid foam sponge reservoir media, having opposing outermost and discharge endwalls, comprehensively enclosed by said film-envelope; and an axially penetratable cannula comprised of a needle body having a disc-butted end and a sharp-pointed end opposite one another, and a strategically placed side-vented discharge inlet perforation within the needle body, said cannula proportionally and centrically disposed internally of said foam sponge;
whereby said syringe facilitates an outermost endwall to discharge endwall, wholly maximal, axial compression there in between, compelling said needle to slidably penetrate projectedly there through to immediate tissue implantation per resultant simultaneous, thru-needle conductive total discharge of the injectant content.

2. The invention of claim 1 further comprising a snugly-constrictive finger ring having opposing ends which are fused to the periphery of the outermost endwall surface to facilitate digitally-engaged manipulation of the instant device.

3. The invention of claim 1 further comprising an antiseptic-impregnated, mucilaginous media contactively adhered to the surface of the discharge endwall to topically disseminate said antiseptic upon semi-adherable, epidermally contactive exposure, and having a stripable evaporation preventive cover film seal overlaying said mucilaginous media.

* * * * *